(12) United States Patent
Litvak et al.

(10) Patent No.: US 8,914,124 B2
(45) Date of Patent: Dec. 16, 2014

(54) TONALITY-BASED OPTIMIZATION OF SOUND SENSATION FOR A COCHLEAR IMPLANT PATIENT

(71) Applicant: Advanced Bionics AG, Staefa (CH)

(72) Inventors: Leonid M. Litvak, Los Angeles, CA (US); Abhijit Kulkarni, Newbury Park, CA (US)

(73) Assignee: Advanced Bionics AG, Staefa (CH)

( * ) Notice: Subject to any disclaimer, the term of this patent is extended or adjusted under 35 U.S.C. 154(b) by 108 days.

(21) Appl. No.: 13/799,575

(22) Filed: Mar. 13, 2013

(65) Prior Publication Data

US 2013/0197606 A1    Aug. 1, 2013

Related U.S. Application Data

(62) Division of application No. 12/172,869, filed on Jul. 14, 2008, now Pat. No. 8,412,340.

(60) Provisional application No. 60/949,815, filed on Jul. 13, 2007.

(51) Int. Cl.
*A61N 1/05* (2006.01)
*A61N 1/36* (2006.01)

(52) U.S. Cl.
CPC ........... *A61N 1/36032* (2013.01); *A61N 1/0541* (2013.01); *H04R 2225/67* (2013.01)
USPC ................ 607/55; 607/56; 607/57; 607/136; 607/137

(58) Field of Classification Search
CPC .................. A61N 1/36032; A61N 1/0541
USPC ...................... 607/55–57, 136–137
See application file for complete search history.

(56) References Cited

U.S. PATENT DOCUMENTS

| 4,819,647 | A | | 4/1989 | Byers et al. |
| 5,601,617 | A | * | 2/1997 | Loeb et al. ..................... 607/56 |
| RE36,714 | E | | 5/2000 | Brandenburg et al. |
| 6,129,753 | A | | 10/2000 | Kuzma |
| 6,219,580 | B1 | | 4/2001 | Faltys et al. |
| 6,272,382 | B1 | | 8/2001 | Faltys et al. |
| 6,308,101 | B1 | | 10/2001 | Faltys et al. |
| 7,081,581 | B2 | | 7/2006 | Allamanche et al. |
| 7,251,530 | B1 | | 7/2007 | Overstreet et al. |
| 7,729,775 | B1 | | 6/2010 | Saoji et al. |

(Continued)

OTHER PUBLICATIONS

Zeng, et al., "Cochlear Implants: System Design, Integration, and Evaluation", Reviews in Biomedical Engineering, vol. 1, 2008.
Gao, et al., "A Novel Speech-Processing Strategy Incorporating Tonal Information for Cochlear Implants", Transactions on Biomedical Engineering, vol. 51, Issue 5, May 2004.
International Search Report and Written Opinion received in International Application No. PCT/US2009/050212, dated Sep. 21, 2009.

(Continued)

*Primary Examiner* — Christopher D Koharski
*Assistant Examiner* — Natasha Patel
(74) *Attorney, Agent, or Firm* — ALG Intellectual Property, LLC

(57) ABSTRACT

An exemplary system includes a sound processor configured to 1) divide an audio signal into a plurality of analysis channels and 2) generate one or more tonality indices each representing a tonality of one of the analysis channels, and an implantable cochlear stimulator communicatively coupled to the sound processor and configured to 1) generate one or more stimulation pulses configured to represent the audio signal in accordance with one or more stimulation parameters, and 2) adjust the one or more stimulation parameters based on at least one of the tonality indices.

20 Claims, 11 Drawing Sheets

(56) References Cited

U.S. PATENT DOCUMENTS

| | | |
|---|---|---|
| 2003/0167077 A1* | 9/2003 | Blamey et al. .................. 607/57 |
| 2005/0107843 A1 | 5/2005 | McDermott et al. |
| 2006/0052841 A1* | 3/2006 | Daly et al. ...................... 607/57 |
| 2006/0100672 A1 | 5/2006 | Litvak |
| 2006/0247735 A1 | 11/2006 | Honert |
| 2009/0012580 A1 | 1/2009 | Arnoldner et al. |

OTHER PUBLICATIONS

Non-Final Office Action received in U.S. Appl. No. 12/172,869, Sep. 27, 2011.

Non-Final Office Action received in U.S. Appl. No. 12/172,869, dated Mar. 1, 2012.

Non-Final Office Action received in U.S. Appl. No. 12/172,869, dated Jul. 18, 2012.

* cited by examiner

TONALITY-BASED OPTIMIZATION OF SOUND SENSATION FOR A COCHLEAR IMPLANT PATIENT

RELATED APPLICATIONS

The present application is a divisional application of U.S. patent application Ser. No. 12/172,869, filed Jul. 14, 2008, which application claims the benefit of U.S. Provisional Patent Application No. 60/949,815, filed on Jul. 13, 2007. Both applications are incorporated herein by reference in their entireties.

BACKGROUND INFORMATION

The sense of hearing in human beings involves the use of hair cells in the cochlea that convert or transduce acoustic signals into auditory nerve impulses. Hearing loss, which may be due to many different causes, is generally of two types: conductive and sensorineural. Conductive hearing loss occurs when the normal mechanical pathways for sound to reach the hair cells in the cochlea are impeded. These sound pathways may be impeded, for example, by damage to the auditory ossicles. Conductive hearing loss may often be helped by the use of conventional hearing aids that amplify sound so that acoustic signals reach the cochlea and the hair cells. Some types of conductive hearing loss may also be treated by surgical procedures.

Sensorineural hearing loss, on the other hand, is due to the absence or the destruction of the hair cells in the cochlea which are needed to transduce acoustic signals into auditory nerve impulses. Thus, many people who suffer from severe to profound sensorineural hearing loss are unable to derive any benefit from conventional hearing aid systems.

To overcome sensorineural hearing loss, numerous cochlear implant systems—or cochlear prosthesis—have been developed. Cochlear implant systems bypass the hair cells in the cochlea by presenting electrical stimulation directly to the auditory nerve fibers. Direct stimulation of the auditory nerve fibers leads to the perception of sound in the brain and at least partial restoration of hearing function. To facilitate direct stimulation of the auditory nerve fibers, an array of electrodes may be implanted in the cochlea. The electrodes form a number of stimulation channels through which electrical stimulation pulses may be applied directly to auditory nerves within the cochlea.

Hence, an audio signal may be presented to a patient by processing and translating the audio signal into a number of electrical stimulation pulses. The stimulation pulses may then be applied directly to auditory nerves within the cochlea via one or more of the stimulation channels.

Many audio signals include both tonal and noise components. Tonal components are those that have a clear sense of pitch to them, whereas the noise components sound atonal. Examples of tonal sounds may include a flute sound, or a singer singing a vowel. Background noise is usually atonal. Many real sounds are a mixture of tonal and noise components. However, it is often difficult for a cochlear implant patient to distinguish between the tonal and noise components of an audio signal.

SUMMARY

Methods of optimizing sound sensation of a cochlear implant patient include dividing an audio signal into a plurality of analysis channels, generating one or more tonality indices each representing a tonality of one of the analysis channels, generating one or more stimulation pulses configured to represent the audio signal in accordance with one or more stimulation parameters, and adjusting at least one of the stimulation parameters based on at least one of the tonality indices.

Systems for optimizing sound sensation of a cochlear implant patient include an implantable cochlear stimulator communicatively coupled to a sound processor. The sound processor is configured to divide an audio signal into a plurality of analysis channels and generate one or more tonality indices each representing a tonality of one of the analysis channels. The implantable cochlear stimulator is configured to generate one or more stimulation pulses configured to represent the audio signal in accordance with one or more stimulation parameters and adjust at least one of the stimulation parameters based on at least one of the tonality indices.

BRIEF DESCRIPTION OF THE DRAWINGS

The accompanying drawings illustrate various embodiments of the principles described herein and are a part of the specification. The illustrated embodiments are merely examples and do not limit the scope of the disclosure.

Throughout the drawings, identical reference numbers designate similar, but not necessarily identical, elements.

DETAILED DESCRIPTION

Methods and systems for optimizing sound sensation of a cochlear implant patient based on a tonality of an audio signal are described herein. In some examples, a sound processor is configured to divide an audio signal into a plurality of analysis channels and generate one or more tonality indices each representing a tonality of one of the analysis channels. An implantable cochlear stimulator is communicatively coupled to the sound processor and configured to generate one or more stimulation pulses configured to represent the audio signal in accordance with one or more stimulation parameters. The implantable cochlear stimulator is further configured to adjust at least one of the stimulation parameters based on at least one of the tonality indices. For example, the implantable cochlear stimulator may dynamically increase a focusing of an excitation field created by the stimulation pulses and/or decrease a stimulation rate of the stimulation pulses in response to a portion of an audio signal that is more tonal than noisy. Alternatively, the implantable cochlear stimulator may dynamically decrease a focusing of an excitation field created by the stimulation pulses and/or increase a stimulation rate of the stimulation pulses in response to a portion of an audio signal that is more noisy than tonal.

In the following description, for purposes of explanation, numerous specific details are set forth in order to provide a thorough understanding of the present systems and methods. It will be apparent, however, to one skilled in the art that the present systems and methods may be practiced without these specific details. Reference in the specification to "one embodiment" or "an embodiment" means that a particular feature, structure, or characteristic described in connection with the embodiment is included in at least one embodiment. The appearance of the phrase "in one embodiment" in various places in the specification are not necessarily all referring to the same embodiment.

Figure 1:
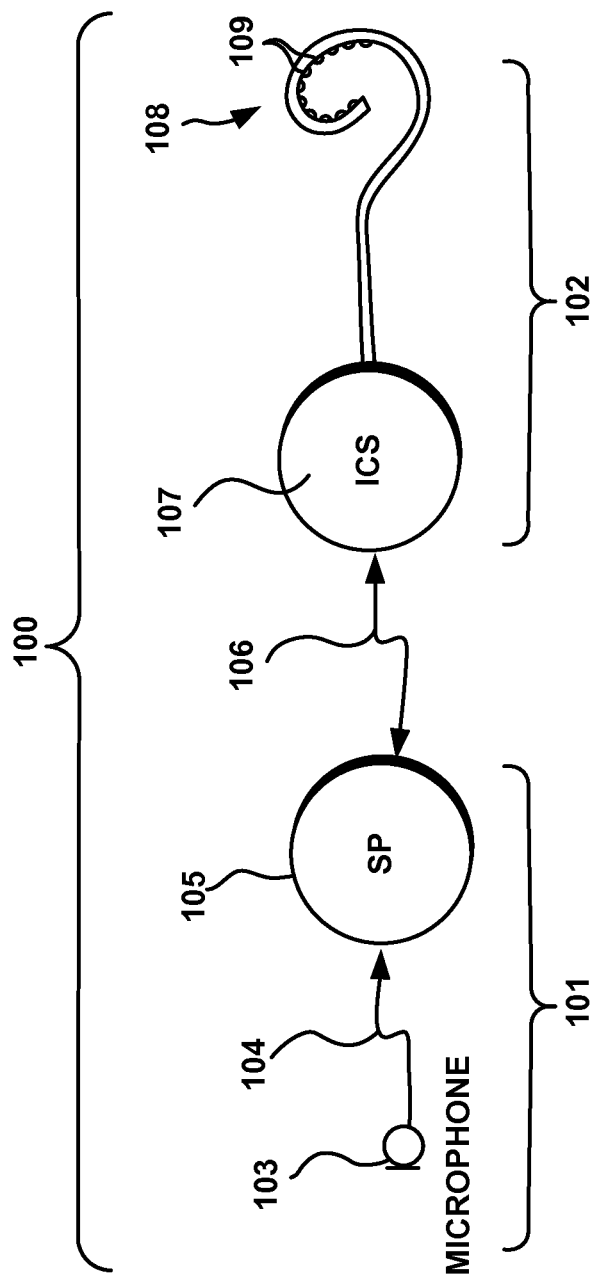
FIG. 1 illustrates an exemplary cochlear implant system according to principles described herein.

FIG. 1 illustrates an exemplary cochlear implant system 100 that may be used in accordance with the present methods and systems. Exemplary cochlear implant systems suitable for use as described herein include, but are not limited to, those disclosed in U.S. Pat. Nos. 6,219,580; 6,272,382; and 6,308,101, all of which are incorporated herein by reference in their respective entireties. The cochlear implant system 100 of FIG. 1 includes a sound processor portion 101 and a cochlear stimulation portion 102. The sound processor portion 101 may include a sound processor 105, a microphone 103, and/or additional circuitry as best serves a particular application. The cochlear stimulation portion 102 may include an implantable cochlear stimulator 107, a number of electrodes 109 disposed on a lead 108, and/or additional circuitry as best serves a particular application. The components within the sound processor portion 101 and the cochlear stimulation portion 102 will be described in more detail below.

The microphone 103 of FIG. 1 is configured to sense acoustic signals and convert the sensed signals to corresponding electrical signals. The electrical signals are sent from the microphone 103 to the sound processor 105 via a communication link 104. Alternatively, the microphone 103 may be connected directly to, or integrated with, the sound processor 105. The sound processor 105 processes these converted acoustic signals in accordance with a selected sound processing strategy to generate appropriate stimulation parameters for controlling the implantable cochlear stimulator 107. These stimulation parameters control signals may specify or define the polarity, magnitude, location (i.e., which electrode pair or electrode group receive the stimulation current), stimulation rate, timing (i.e., when the stimulation current is to be applied to a particular electrode pair), and/or any other characteristic of the stimulation current that is generated by the implantable cochlear stimulator 107.

The lead 108 shown in FIG. 1 is configured to be inserted within a duct of the cochlea. As shown in FIG. 1, the lead 108 includes a multiplicity of electrodes 109, e.g., sixteen electrodes, spaced along its length. It will be understood, however, that any number of electrodes 109 may be disposed on the lead 108. The lead 108 may be substantially as shown and described in U.S. Pat. No. 4,819,647 or 6,129,753, each of which is incorporated herein by reference in its respective entirety. As will be described in more detail below, electronic circuitry within the implantable cochlear stimulator 107 is configured to generate and apply stimulation current to the cochlea via selected stimulation channels (i.e., pairs or groups of the individual electrodes 109) in accordance with a specified stimulation pattern defined by the sound processor 105.

The implantable cochlear stimulator 107 and the sound processor 105 may be electronically connected via a suitable data or communication link 106. It will be understood that the data communication link 106 may include a bi-directional communication link and/or one or more dedicated uni-directional communication links.

In some examples, the sound processor 105 and the microphone 103 comprise an external portion of the cochlear implant system 100 and the implantable cochlear stimulator 107 and the electrode lead 108 comprise an implantable portion of the system 100 that is implanted within a patient's body. In alternative embodiments, one or more portions of the sound processor 105 are included within the implantable portion of the cochlear implant system 100.

The external and implantable portions of the cochlear implant system 100 may each include one or more coils configured to transmit and receive power and/or control signals via the communication link 106. For example, the external portion of the cochlear implant system 100 may include an external coil (not shown) and the implantable portion of the cochlear implant system 100 may include an implantable coil (not shown). The external coil and the implantable coil may be inductively coupled to each other, thereby allowing data to be transmitted therebetween. The data may include, for example, the magnitude and polarity of a sensed acoustic signal. The external coil may also transmit power from the external portion to the implantable portion of the cochlear implant system 100. It will be noted that, in some embodiments, both the sound processor 105 and the implantable cochlear stimulator 107 may be implanted within the patient, either in the same housing or in separate housings. If the sound processor 105 and the implantable cochlear stimulator 107 are in the same housing, the communication link 106 may be realized with a direct wire connection within such housing. If the sound processor 105 and the implantable cochlear stimulator 107 are in separate housings, the communication link 106 may include one or more inductive links, for example.

Figure 2:
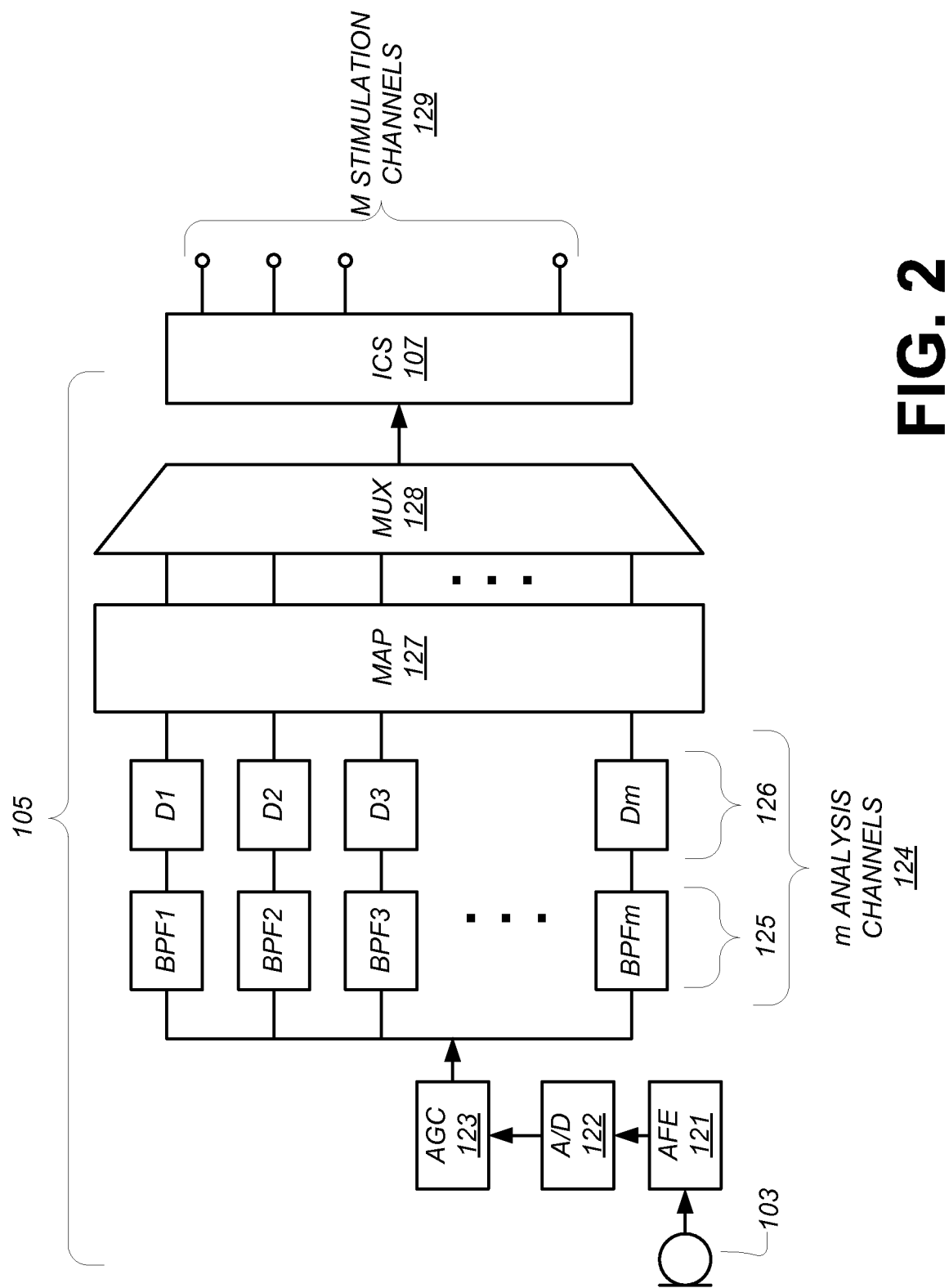
FIG. 2 is a functional block diagram of an exemplary sound processor and implantable cochlear stimulator according to principles described herein.

FIG. 2 is a functional block diagram of an exemplary sound processor 105 and implantable cochlear stimulator 107. The functions shown in FIG. 2 are merely representative of the many different functions that may be performed by the sound processor 105 and/or the implantable cochlear stimulator 107. A more complete description of the functional block diagram of the sound processor 105 and the implantable cochlear stimulator 107 is found in U.S. Pat. No. 6,219,580, which is incorporated herein by reference in its entirety.

As shown in FIG. 2, the microphone 103 senses acoustic information, such as speech and music, and converts the acoustic information into one or more electrical signals. These signals are then amplified in audio front-end (AFE) circuitry 121. The amplified audio signal is then converted to a digital signal by an analog-to-digital (A/D) converter 122.

The resulting digital signal is then subjected to automatic gain control using a suitable automatic gain control (AGC) function 123. In some examples, a pre-emphasis stage may be included that is configured to shape the spectrum of the signals to remove low-frequency noise from the signals.

After appropriate automatic gain control, the digital signal is then processed in one of a number of digital signal processing or analysis channels 124. For example, the sound processor 105 may include, but is not limited to, eight analysis channels 124. Each analysis channel 124 may respond to a different frequency content of the sensed acoustical signal. In other words, each analysis channel 124 includes a band-pass filter (BPF1-BPFm) 125 or other type of filter such that the digital signal is divided into m analysis channels 124. The lowest frequency filter may be a low-pass filter, and the highest frequency filter may be a high-pass filter.

As shown in FIG. 2, each of the m analysis channels 124 may also include an energy detection stage (D1-Dm) 126. Each energy detection stage 126 may include any combination of circuitry configured to detect the amount of energy contained within each of the m analysis channels 124. For example, each energy detection stage 126 may include a rectification circuit followed by an integrator circuit.

After energy detection, the signals within each of the m analysis channels 124 are forwarded to a mapping stage 127. The mapping stage 127 is configured to map the signals in each of the m analysis channels 124 to one or more of M stimulation channels 129. In other words, the information contained in the m analysis channels 124 is used to define the stimulation current pulses that are applied to the patient by the implantable cochlear stimulator 107 via the M stimulation channels 129. As mentioned previously, pairs or groups of individual electrodes 109 make up the M stimulation channels.

In some examples, the mapped signals are serialized by a multiplexer 128 and transmitted to the implantable cochlear stimulator 107. The implantable cochlear stimulator 107 may then apply stimulation current via one or more of the M stimulation channels 129 to one or more stimulation sites within the patient's cochlea. As used herein and in the appended claims, the term "stimulation site" will be used to refer to a target area or location at which the stimulation current is applied. For example, a stimulation site may refer to a particular location within the cochlea. Through appropriate weighting and sharing of currents between the electrodes 109, stimulation current may be applied to any stimulation site along the length of the lead 108.

Figure 3:
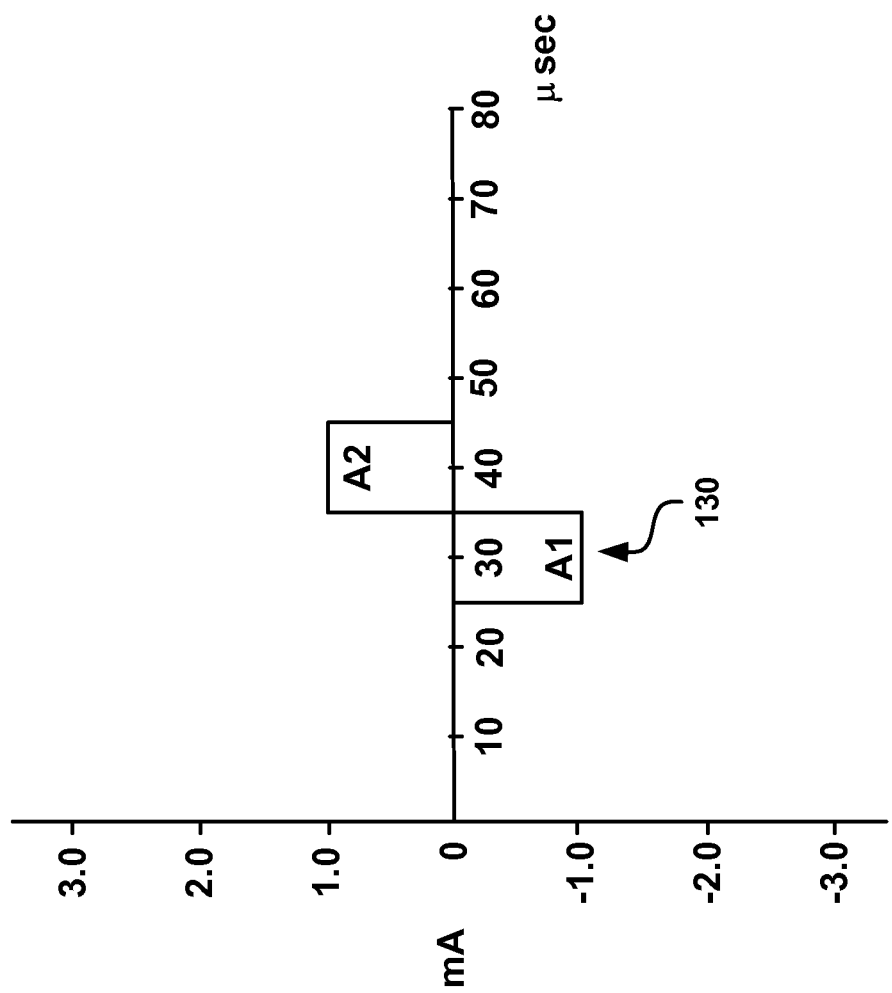
FIG. 3 illustrates an exemplary stimulation current pulse that may be delivered to neural tissue via one or more of the stimulation channels according to principles described herein.

FIG. 3 illustrates an exemplary stimulation current pulse 130 that may be delivered to neural tissue via one or more of the stimulation channels 129. The stimulation current pulse 130 of FIG. 3 is biphasic. In other words, the pulse 130 includes two parts—a negative first phase having an area A1 and a positive second phase having an area A2. In some implementations, the negative phase A1 causes neural tissue to depolarize or fire. The biphasic stimulation pulse 130 shown in FIG. 3 has an amplitude of 1 milliamp (mA) and a pulse width of 20 microseconds (μsec) for illustrative purposes only. It will be recognized that any of the characteristics of the stimulation pulse 130, including, but not limited to, the pulse shape, amplitude, pulse width, frequency, burst pattern (e.g., burst on time and burst off time), duty cycle or burst repeat interval, ramp on time, and ramp off time may vary as best serves a particular application. Moreover, the characteristics of the stimulation pulse 130 may be defined by the sound processor 105 as best serves a particular application.

The biphasic stimulation pulse 130 shown in FIG. 3 is "charge balanced" because the negative area A1 is equal to the positive area A2. A charge-balanced biphasic pulse is often employed as the stimulus to minimize electrode corrosion and charge build-up which can harm surrounding tissue. However, it will be recognized that the biphasic stimulation pulse 130 may alternatively be charge-imbalanced as best serves a particular application.

As mentioned, an audio signal that may be presented to a cochlear implant patient may include both tonal and noise components. As used herein, a "tonal component" refers to one or more portions of an audio signal that, if sounded by themselves, would convey a sense of pitch. For example, sound of a flute has strong tonal components. A "noise component" refers to a portions of an audio signal that does not have a strong associated pitch. For example, car noise is composed primarily of "noise components." Sounds such as human speech contain both "tonal" and "noise" components. For example, many fricative consonants are composed of "noise" components, whereas some vowels have "tonal" components, especially in the lower frequencies.

Figure 4:
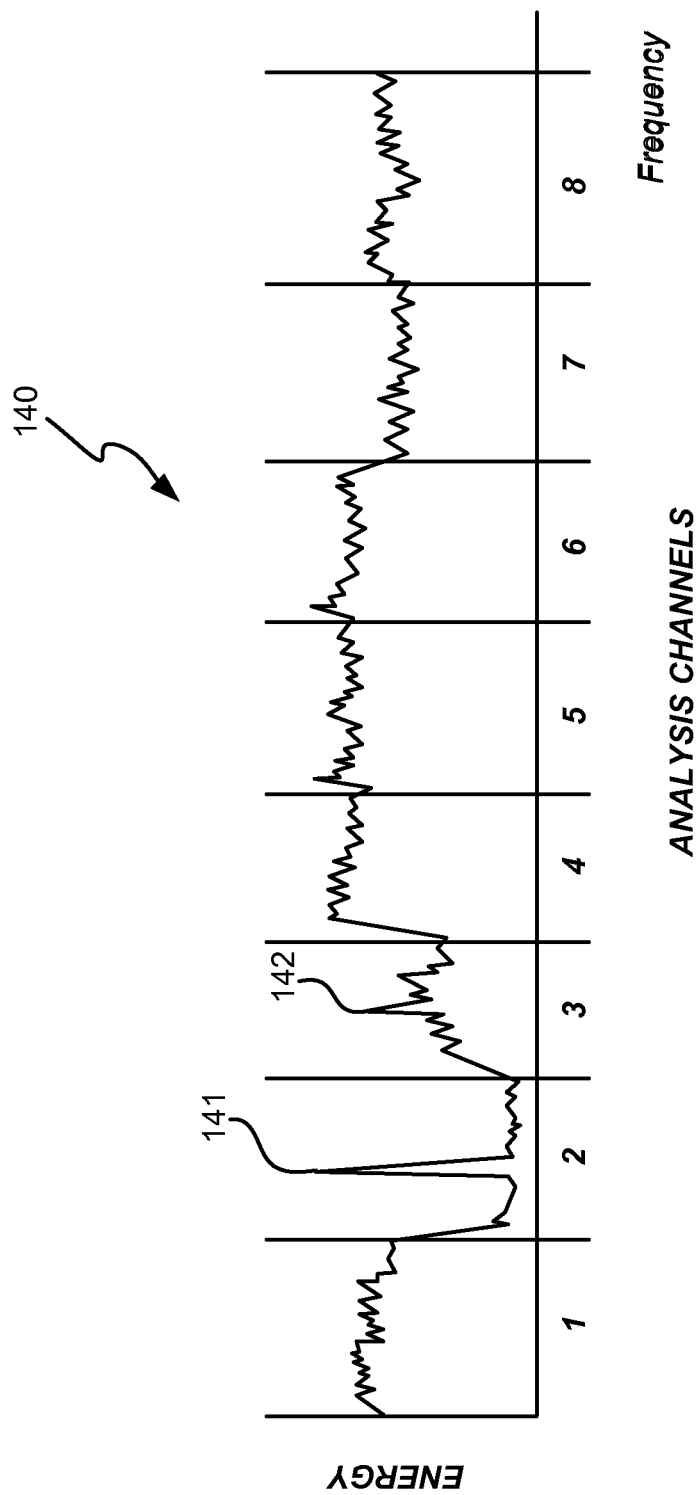
FIG. 4 illustrates an exemplary audio signal in the frequency domain that may be presented to a cochlear implant patient during a particular time period or stimulation frame according to principles described herein.

In the frequency domain, tonal components of an audio signal are represented by relatively strong spectral peaks and noise components are represented by relatively flat spectral energy levels. For example, FIG. 4 illustrates an exemplary audio signal 140 in the frequency domain that may be presented to a cochlear implant patient during a particular time period or stimulation frame. As shown in FIG. 4, the audio signal 140 may be divided into eight analysis channels 124. It will be recognized that the audio signal 140 may be divided into any number of analysis channels 124 as may serve a particular application. In some examples, each analysis channel 124 shown in FIG. 4 is mapped to one of the stimulation channels 129 shown in FIG. 2.

The vertical axis in FIG. 4 represents the amount of signal energy contained within each analysis channel 124. As shown in FIG. 4, each analysis channel 124 contains varying energy levels. In addition, channels may differ in the frequency domain distribution of the energy within a channel. By analyzing the frequency domain energy distribution within each analysis channel 124, a "tonality index" representing the tonality of each channel 124 may be determined. To illustrate, the second analysis channel 124 shown in FIG. 4 includes a relatively strong spectral peak 141, and would therefore have a relatively high tonality index. The third analysis channel 124 shown in FIG. 4 includes a relatively medium-strength spectral peak 142, and would therefore have a tonality index proportionally lower than that of the second analysis channel 124. The seventh analysis channel 124 includes a relatively flat spectral energy level, and would therefore have a relatively low tonality index. Various methods of determining the tonality index for each analysis channel 124 will be described in more detail below.

In some examples, as will be described in more detail below, the stimulation parameters may be dynamically adjusted in accordance with the determined tonality indices in order to optimize the quality (i.e., accuracy) of the sound sensation of the audio signal as perceived by the cochlear implant patient. It has been shown that the quality of the sound sensation can depend on the configuration of the electrodes 109 and/or the stimulation rate at which the electrical stimulation pulses are applied to a stimulation site via the electrodes 109. For example, decreasing the stimulation rate and using a multipolar (as opposed to monopolar) electrode configuration may produce a sound that is more tonal than noise-like. Likewise, increasing the stimulation rate and using a more monopolar electrode configuration may increase the quality of sound sensation of a sound that is more noise-like than tonal.

Hence, the systems and methods described herein may be configured to improve the quality of sound sensation of an audio signal by dynamically adjusting the electrode configuration and/or stimulation rate at which electrical stimulation pulses are applied to a stimulation site as the tonality of the audio signal changes over time.

In some examples, an electrode configuration may be adjusted by using a multipolar electrode configuration to focus or narrow excitation fields generated by the implantable cochlear stimulator 107. In a multipolar electrode configuration, one or more additional electrodes are provided through which compensating current is delivered. These additional electrodes will be referred to herein as "compensating electrodes."

Figure 5:
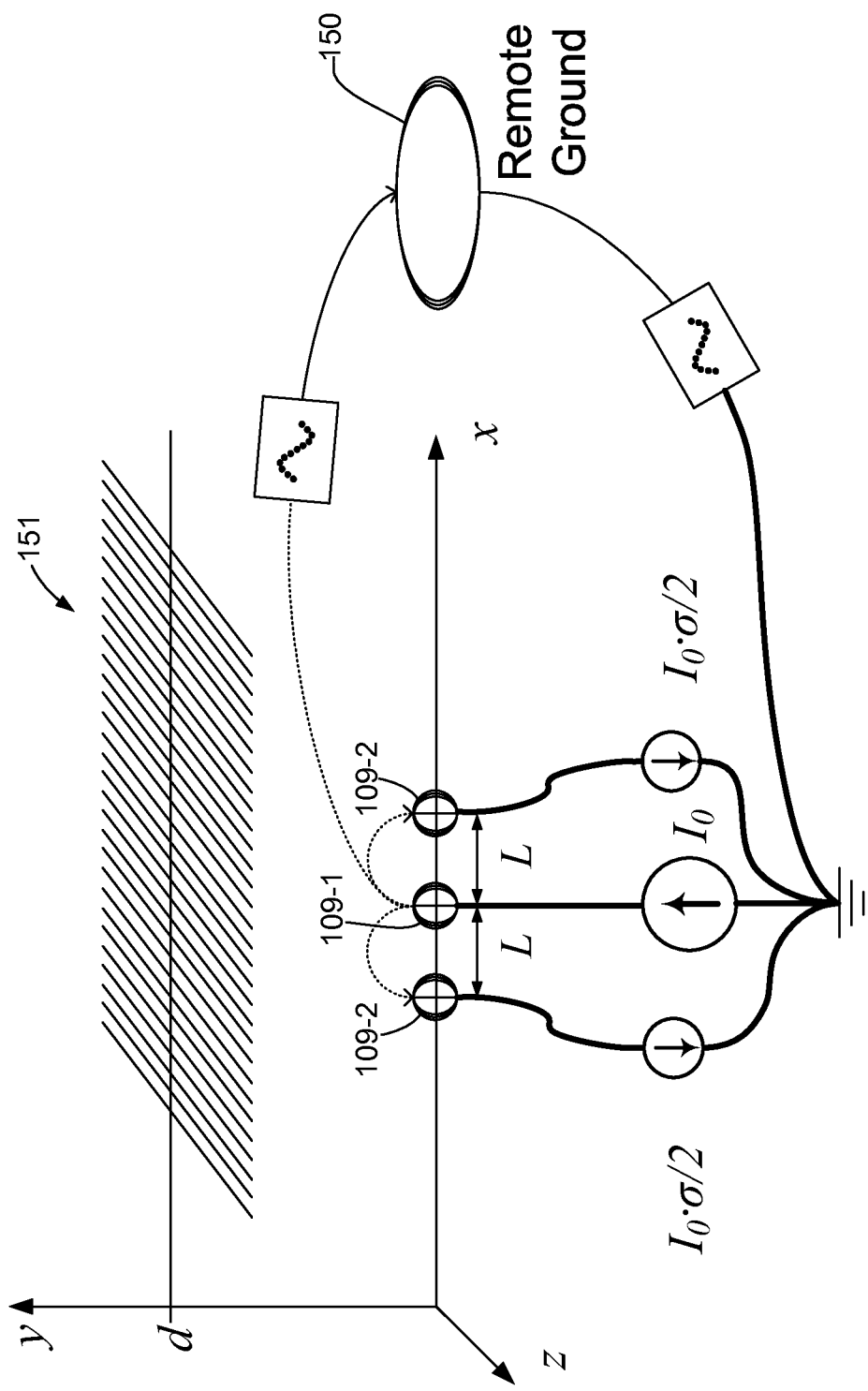
FIG. 5 illustrates an exemplary multipolar electrode configuration according to principles described herein.

FIG. 5 illustrates an exemplary multipolar electrode configuration that may be used in connection with the systems and methods described herein. As shown in FIG. 5, the multipolar electrode configuration includes a stimulating electrode 109-1, compensating electrodes 109-2, and a remote ground electrode 150 configured to provide a return path for the current delivered by the electrodes 109-1 and 109-2. Electrodes 109-1 and 109-2 will be referred to collectively as "electrodes 109" for ease of explanation.

The particular multipolar configuration shown in FIG. 5 may be referred to as "tripolar" or as "quadripolar" because, for a given stimulation site, three electrodes 109 are engaged simultaneously, in addition the remote ground electrode 150. The polarity of electrode 109-1 may be configured as anodic (+) and the polarity of compensating electrodes 109-2 may be configured as cathodic (−), or vice versa. It will be understood that the number of electrodes 109 within the multipolar configuration may vary as may serve a particular application. Alternative multipolar configurations will be described in more detail below. However, for illustrative purposes only, it will be assumed in many of the examples given herein that the multipolar configuration is tripolar.

In some examples, the electrodes 109 are positioned a certain distance d away from a stimulation site 151 (e.g., a location within the cochlea). However, it will be recognized that each electrode 109 may be positioned at different distances from the stimulation site 151. Moreover, as shown in FIG. 5, the electrodes 109 may be separated one from another by a separation distance L. The separation distance L and the distance d may vary as may serve a particular application. It will also be recognized that the electrodes 109 may be positioned in any alternative arrangement as may serve a particular application. For example, the electrodes 109 may be located within different planes.

As shown in FIG. 5, a stimulation current $I_0$ may be applied to the stimulation site 151 via the center electrode 109-1. The stimulation current $I_0$ may be generated by the stimulator 100 and may be in accordance with one or more stimulation parameters as may serve a particular application.

As shown in FIG. 5, current may also be applied via the compensating electrodes 109-2 in order to narrow or focus the excitation field caused by the center electrode 109-1. The compensating current is opposite in phase as the stimulation current $I_0$ and may be represented by $I_0*\sigma/2$, wherein $\sigma$ represents a programmable multiplication factor ranging from 0 to 1. Hence, the total compensating current applied via electrodes 109-2 may be varied from 0 to $I_0$. The programmable multiplication factor $\sigma$ will be referred to herein as a "focusing factor."

For example, the focusing factor $\sigma$ may be set to 0 in order to prevent current from being applied via the compensating electrodes 109-2. In this manner, the center electrode 109-1 may be configured to apply current in a fully monopolar configuration. The focusing factor $\sigma$ may be programmed to be equal to 1 in order to apply an equal amount of current via the compensating electrodes 109-2 as is applied via the center electrode 109-1. In this manner, the electrodes 109 may be configured to operate in a fully multipolar configuration.

In some examples, the electrodes 109 may be programmed to operate in a "partially multipolar" configuration wherein the total amount of current applied by the compensating electrodes 109-2 is greater than 0 and less than $I_0$. The term "multipolar" will be used herein to generally refer to fully multipolar and partially multipolar configurations, unless otherwise specified.

The compensating electrodes 109-2 shown in FIG. 5 are both configured to apply an equal amount of compensating current (i.e., $I*\sigma/2$) for illustrative purposes only. It will be recognized that the compensating electrodes 109-2 may alternatively be configured to apply different amounts of compensating current as may serve a particular application.

Figure 6:
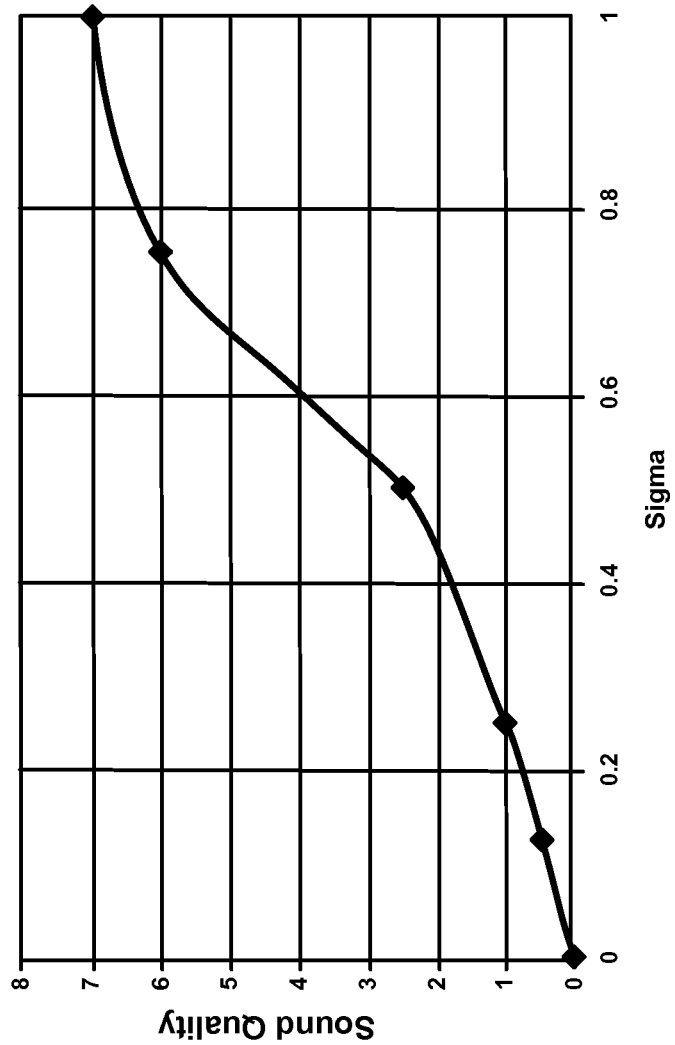
FIG. 6 is a graph illustrating the effect of increasing the focusing factor σ on the sound quality of a relatively tonal sound according to principles described herein.

FIG. 6 is a graph illustrating the effect of increasing the focusing factor $\sigma$ on the sound quality of a relatively tonal sound. As shown in FIG. 6, as the focusing factor $\sigma$ increases, the sound quality also increases.

An electrode configuration may additionally or alternatively be adjusted by using current steering. Current steering may be used in configurations wherein a desired stimulation site is located spatially in between two electrodes 109. To effectively deliver stimulation to the stimulation site, weighted current may be applied simultaneously or in a time-interleaved manner via the two adjacent electrodes 109.

Figure 7:
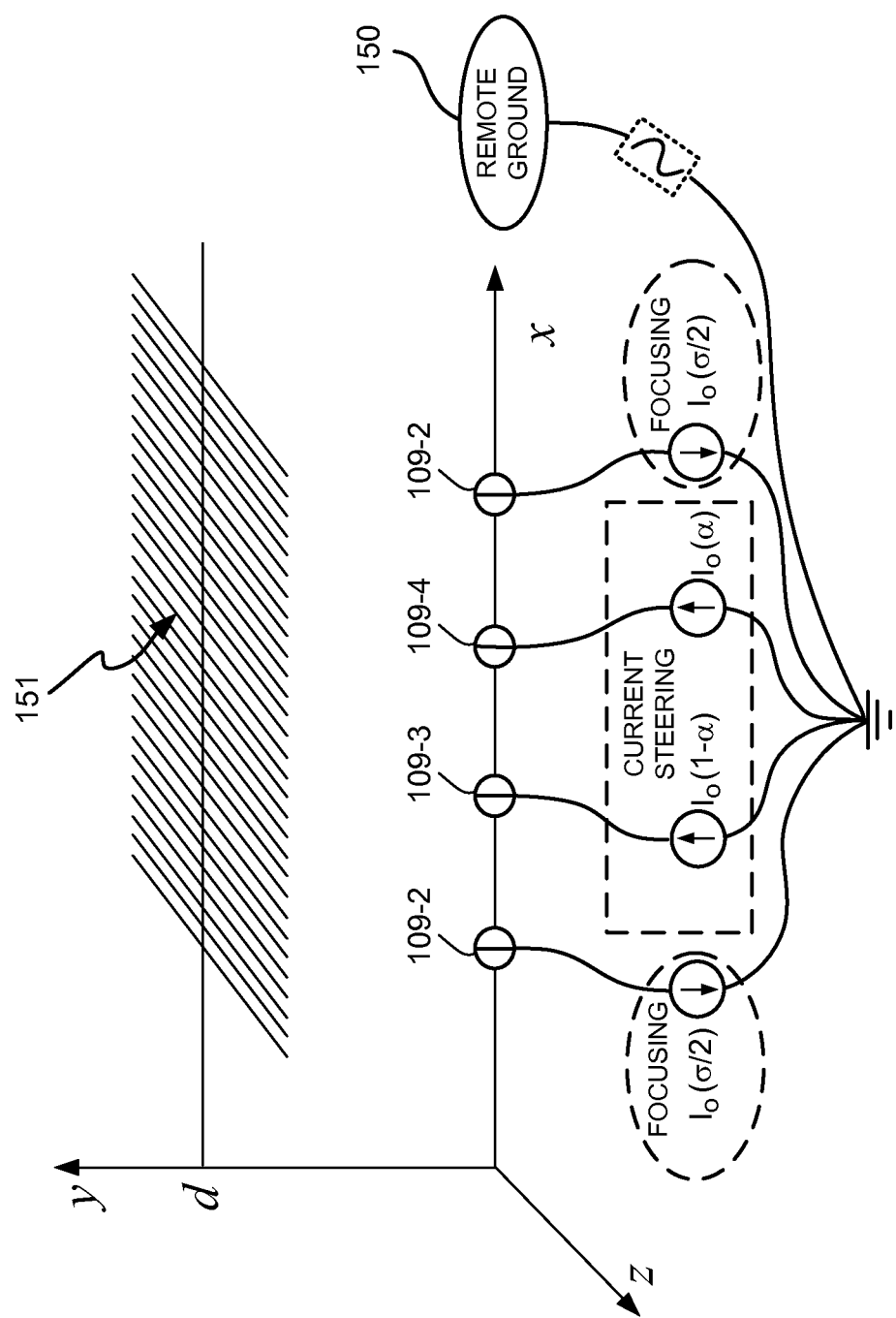
FIG. 7 illustrates a configuration wherein current steering is used in conjunction with the focusing configuration of FIG. 5 to adjust an electrode configuration according to principles described herein.

To illustrate, FIG. 7 illustrates a configuration wherein current steering is used in conjunction with the focusing configuration of FIG. 5 to adjust an electrode configuration. As shown in FIG. 7, electrodes 109-3 and 109-4 may be spatially located in between compensating electrodes 109-2. Weighted current may be applied via electrodes 109-3 and 109-4 to apply stimulation to a stimulation site located in between electrodes 109-3 and 109-4. The weighted current may depend on an adjustable weight factor $\alpha$. In this manner, current steering and focusing may be used to further improve the sound quality and accuracy of a tonal sound.

Figure 8:
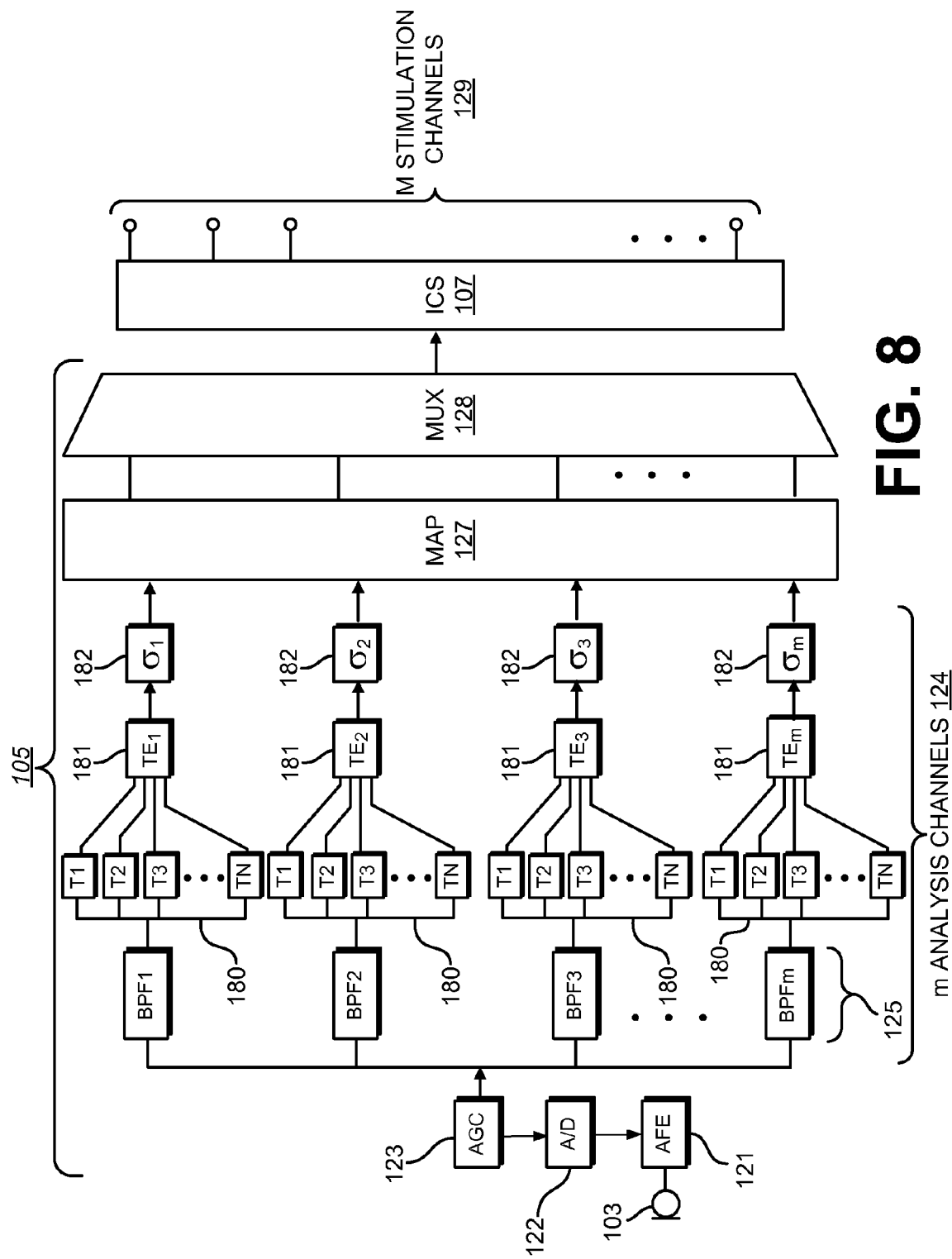
FIG. 8 illustrates a functional block diagram of an exemplary sound processor configured to determine a tonality index for the contents of each analysis channel according to principles described herein.

FIG. 8 illustrates a functional block diagram of an exemplary sound processor 105 configured to determine a tonality index for the contents of each analysis channel 124. As shown in FIG. 8, each analysis channel 124 may be divided into a plurality of sub-band analysis channels 180. The number of sub-band analysis channels 180 within each analysis channel 124 may vary as may serve a particular application. In general, there may be N sub-band analysis channels 180 represented as T1 through TN in FIG. 8. Furthermore, the number of sub-bands N may differ across m analysis channels.

One or more tonal detection stages 181, represented as $TE_1$ through $TE_m$ in FIG. 8, may be included within the sound processor 105 and configured to generate a tonality index for the contents of each analysis channel 124. The tonal detection stages 181 may include any combination of circuitry, hardware, and/or software as may serve a particular application and may be configured to generate the tonality indices in any suitable manner. For example, each tonal detection stage 181 may include a rectification circuit followed by an integrator circuit.

In some examples, the tonal detection stages 181 are configured to measure the spectral energy levels within each sub-band analysis channel 180. The measured spectral energy levels may be then processed using any suitable method or heuristic to derive tonality indices for each of the analysis channels 124. In some examples, tonal and noise components within each sub-band analysis channel 180 may be identified by the tonal detection stages 181 using schemes similar to those utilized in psychoacoustic models used in perceptual coders (e.g., MP3 coders). The tonality indices may use any suitable metric. For example, a tonality index corresponding to the contents of a particular analysis channel 124 may be the ratio of the maximum spectral energy level to the median spectral energy level contained within the analysis channel 124.

It will be recognized that, in some examples, the analysis channels 124 are not divided into sub-band analysis channels 180. In these examples, the tonal detection stages 181 may be configured to analyze signals within the analysis channels 124 directly to determine the tonality indices.

In some examples, one or more focusing factor stages 182 may be configured to map the tonality indices generated by the tonal detection stages 181 to one or more focusing factors $\sigma$. For example, the tonality index generated by the first tonal detection stage $TE_1$ may be mapped to a first focusing factor $\sigma_1$. The tonality indices and/or the focusing factors may then be used by the mapping stage 127 and/or the implantable cochlear stimulator 107 to adjust the stimulation parameters in order to optimize the stimulation applied via the stimulation channels 129.

To illustrate, the tonal detection stages 181 may determine that the contents of a first analysis channel 124 have a relatively high tonality index (i.e., the signal is more tonal within this channel) while the contents of the other analysis channels 124 have a relatively low tonality index (i.e., the signals are more noise-like within these channels). The measured tonality indices may be used to increase focusing for the first stimulation channel 129 and decrease focusing for the other stimulation channels 129. The stimulation rate may also be adjusted (e.g., lowered) to increase the sound quality of the tonal component located within the first analysis channel 124. Alternatively, the stimulation rate may be increased to increase the sound quality of the noisy components located within the other stimulation channels 129. When adjusting focusing or rate parameters, overall current level I will need to be compensated to maintain equivalent loudness. For adjusting focusing coefficient $\sigma$, current could be adjusted using the formula $I=I0/(1-K\sigma)$, where I0 and K are patient-specific parameters that will be determined by the clinician during the fitting of the strategy. However, the precise formula for current adjustment may vary as may serve a particular application.

Figure 9:
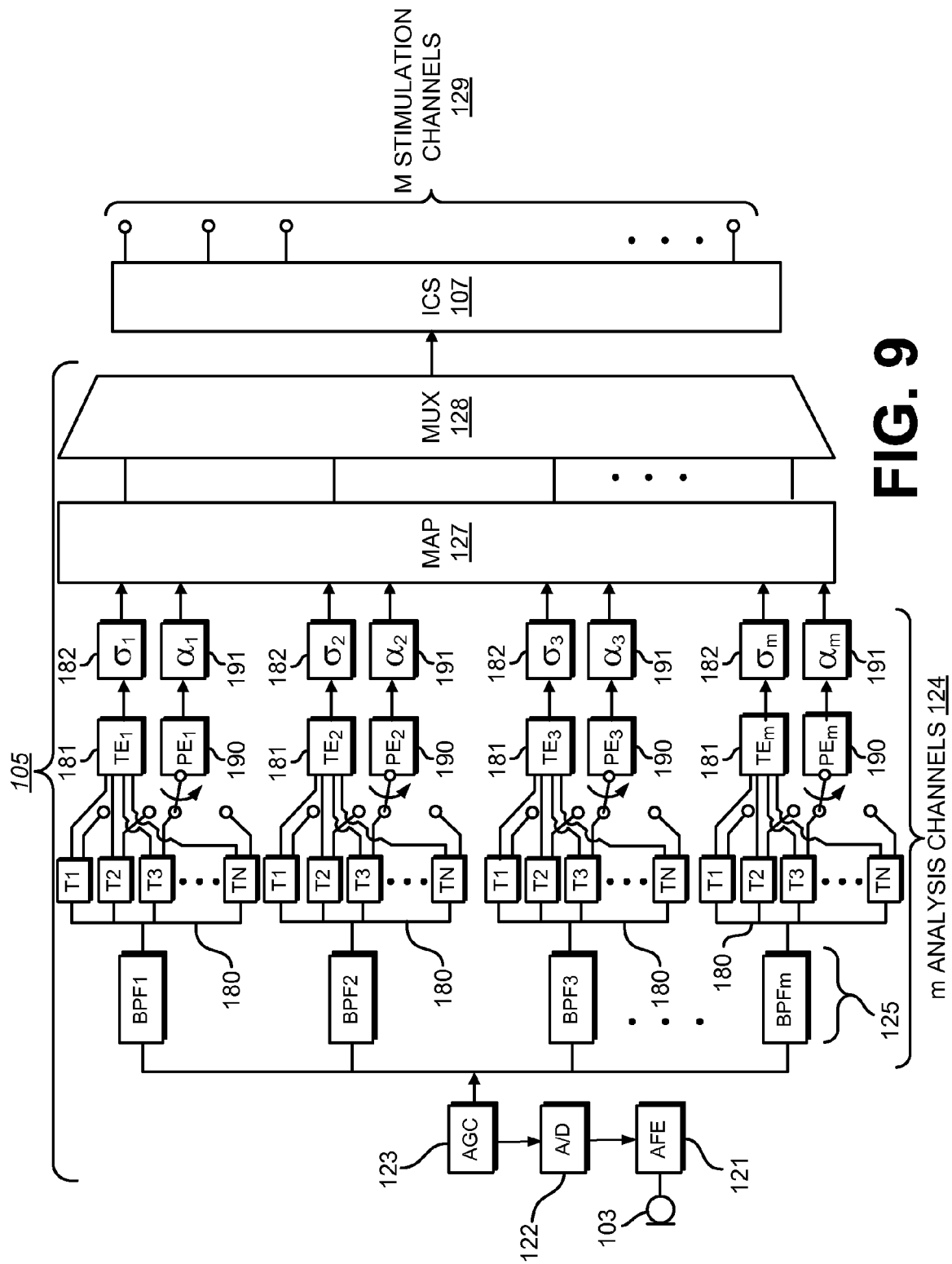
FIG. 9 illustrates a functional block diagram of an exemplary sound processor configured to determine both a tonality index and a peak estimate for the contents of each analysis channel according to principles described herein.

FIG. 9 illustrates a functional block diagram of an exemplary sound processor 105 configured to determine both a tonality index and a peak estimate for the contents of each analysis channel 124. As shown in FIG. 9, each analysis channel 124 may be divided into a plurality of sub-band analysis channels 180. The number of sub-band analysis channels 180 within each analysis channel 124 may vary as may serve a particular application. In general, there may be N sub-band analysis channels 180 represented by T1 through TN in FIG. 9.

The sound processor 105 of FIG. 9 may include one or more tonal detection stages 181 configured to generate a tonality index for the contents of each analysis channel 124 in a manner similar to that described in FIG. 8. In addition, one or more peak estimator stages 190, represented as $PE_1$ through $PE_m$ in FIG. 9, may be included within the sound processor 105 and configured to generate a peak estimate for the contents of each analysis channel 124. The peak estimator stages 190 may include any combination of circuitry, hardware, and/or software as may serve a particular application and may be configured to generate the peak estimates in any suitable manner. For example, the peak estimator stages 190 may be configured to determine the frequency or frequencies at which a spectral energy peak occurs within one or more of the sub-band analysis channels 180.

In some examples, one or more weight factor stages 191 may be configured to map the peak estimates generated by the peak estimator stages 190 to one or more weight factors $\alpha$. For example, the peak estimate generated by the first peak estimator stage $PE_1$ may be mapped to a first weight factor $\alpha_1$. The weight factors $\alpha$ may then be used by the mapping stage 127 and/or the implantable cochlear stimulator 107 to adjust the amount of current steering that is used in order to optimize the stimulation applied via the stimulation channels 129.

Figure 10:
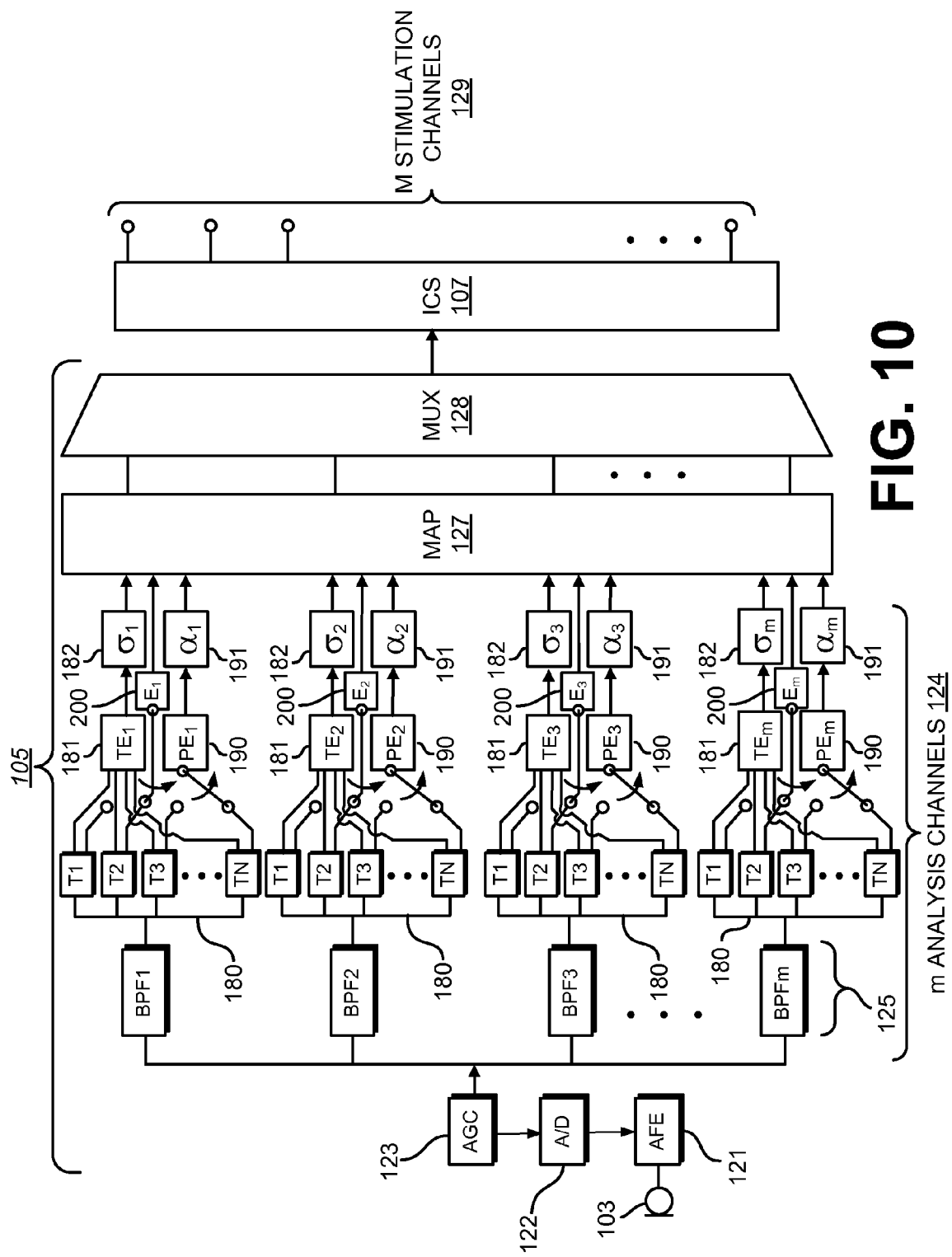
FIG. 10 illustrates a functional block diagram of an exemplary sound processor that is further configured to determine an energy level of the contents of each analysis channel according to principles described herein.

FIG. 10 illustrates a functional block diagram of an exemplary sound processor 105 that is further configured to determine an energy level of the contents of each analysis channel 124. As shown in FIG. 10, each analysis channel 124 may be divided into a plurality of sub-band analysis channels 180. The number of sub-band analysis channels 180 within each analysis channel 124 may vary as may serve a particular application. In general, there may be N sub-band analysis channels 180 represented by T1 through TN in FIG. 10.

The sound processor 105 of FIG. 10 may include one or more tonal detection stages 181 and one or more peak estimator stages 190, as described in FIG. 9. In addition, one or more energy level detection stages 200, represented as $E_1$ through $E_m$ in FIG. 10, may be included within the sound processor 105 and configured to estimate an energy level of the contents of each analysis channel 124. The energy level detection stages 200 may include any combination of circuitry, hardware, and/or software as may serve a particular application and may be configured to detect the energy levels in any suitable manner. The detected energy levels may then be used to adjust the stimulation parameters in order to optimize the stimulation applied via the stimulation channels 129.

It will be recognized that the systems and methods described herein may be used in connection with any stimulation strategy as may serve a particular application. For example, the systems and methods described herein may be used in connection with a stimulation strategy wherein each analysis channel 124 is mapped directly to one of the stimulation channels 129. Alternatively, the systems and methods described herein may be used in connection with an "N-of-M" stimulation strategy wherein a subset of the total number of analysis channels 124 is mapped to the stimulation channels 129. In yet another alternative implementation, the systems and methods described herein may be used in connection with a "continuous interleaved sampling strategy."

Figure 11:
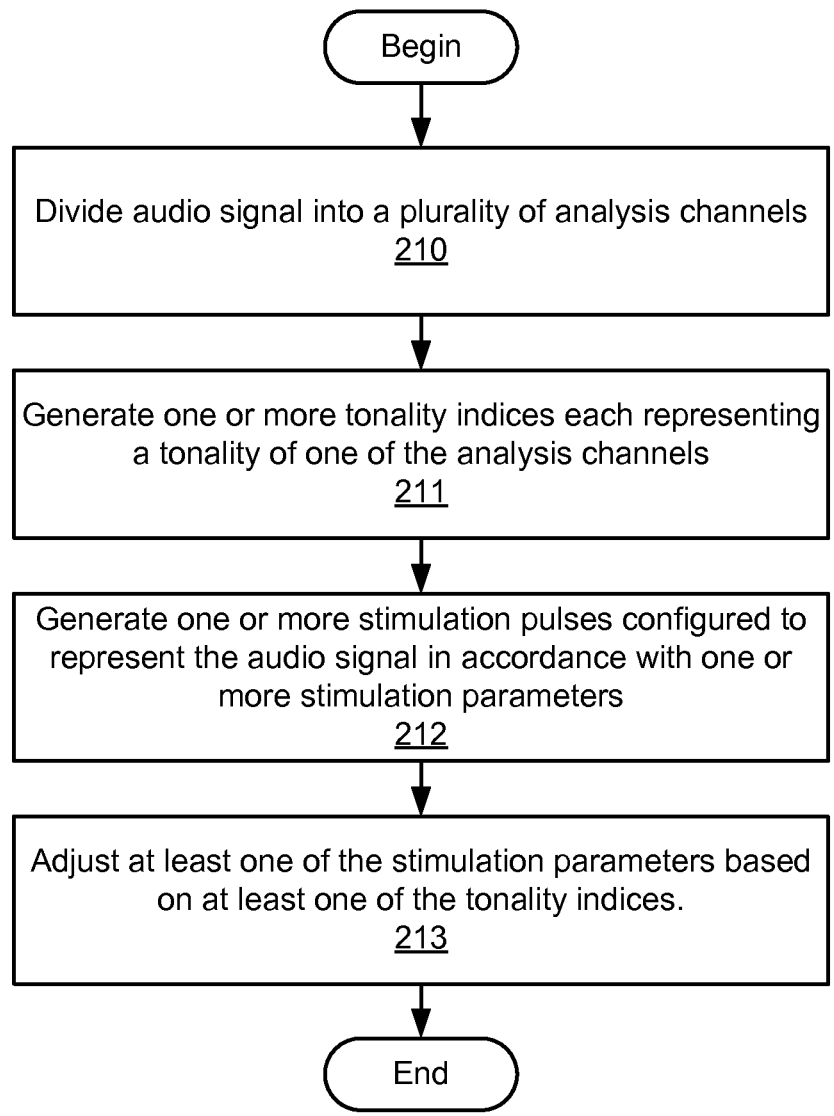
FIG. 11 illustrates an exemplary method of optimizing sound sensation for a cochlear implant patient based on the tonality of an audio signal according to principles described herein.

FIG. 11 illustrates an exemplary method of optimizing sound sensation for a cochlear implant patient based on the tonality of an audio signal. While FIG. 11 illustrates exemplary steps according to one embodiment, other embodiments may omit, add to, reorder, and/or modify any of the steps shown in FIG. 11.

In step 210, an audio signal is divided into a plurality of analysis channels. The audio signal may be divided into a plurality of analysis channels using any of the ways described herein.

In step 211, one or more tonality indices each representing a tonality of one of the analysis channels are generated. The tonality indices may be generated in any of the ways described herein.

In step 212, one or more stimulation pulses configured to represent the audio signal are generated in accordance with one or more stimulation parameters. The stimulation pulses may be generated in any of the ways described herein.

In step 213, at least one of the stimulation parameters is adjusted based on at least one of the tonality indices. For example, an electrode configuration and/or a stimulation rate of the stimulation pulses may be adjusted in any of the ways described herein.

The preceding description has been presented only to illustrate and describe embodiments of the invention. It is not intended to be exhaustive or to limit the invention to any precise form disclosed. Many modifications and variations are possible in light of the above teaching.

What is claimed is:

1. A system comprising:
a sound processor configured to
divide an audio signal into a plurality of analysis channels, and
generate one or more tonality indices each representing a tonality of one of the analysis channels; and
an implantable cochlear stimulator communicatively coupled to the sound processor and configured to
generate one or more stimulation pulses configured to represent the audio signal in accordance with one or more stimulation parameters, and
adjust the one or more stimulation parameters based on at least one of the tonality indices.

2. The system of claim 1, wherein the implantable cochlear stimulator is configured to adjust the one or more stimulation parameters by adjusting an electrode configuration through which the stimulation pulses are applied to a stimulation site.

3. The system of claim 2, wherein the implantable cochlear stimulator is further configured to increase a focusing of an excitation field produced by at least one of the stimulation pulses in response to an increase in at least one of the one or more tonality indices.

4. The system of claim 1, wherein the implantable cochlear stimulator is configured to adjust the one or more stimulation parameters by adjusting a stimulation rate of the one or more stimulation pulses.

5. A system comprising:
a sound processor configured to
divide an audio signal into a plurality of analysis channels each corresponding to a particular electrode included in a plurality of electrodes implanted in a patient, and
generate tonality indices for each of the analysis channels in the plurality of analysis channels, the tonality indices each representing a tonality associated with one of the analysis channels; and
an implantable cochlear stimulator communicatively coupled to the sound processor and configured to generate one or more stimulation pulses configured to represent the audio signal in accordance with one or more stimulation parameters;
wherein the sound processor is further configured to adjust the one or more stimulation parameters based on at least one of the tonality indices.

6. The system of claim 5, wherein the implantable cochlear stimulator is further configured to apply the stimulation pulses to a stimulation site within the patient.

7. The system of claim 6, wherein the stimulation site comprises a location within a cochlea of the patient.

8. The system of claim 5, wherein the sound processor is configured to adjust the one or more stimulation parameters by adjusting an electrode configuration through which the stimulation pulses are applied to the stimulation site.

9. The system of claim 8, wherein the adjusting of the electrode configuration comprises focusing an excitation field produced by at least one of the one or more stimulation pulses.

10. The system of claim 9, wherein the sound processor is further configured to increase the focusing of the excitation field in response to an increase in at least one of the tonality indices.

11. The system of claim 5, wherein the sound processor is further configured to decrease the focusing of the excitation field in response to a decrease in at least one of the tonality indices.

12. The system of claim 8, wherein the adjusting of the electrode configuration comprises adjusting an amount of current steering corresponding to at least one of the one or more stimulation pulses.

13. The system of claim 5, wherein the sound processor is configured to adjust the one or more stimulation parameters by adjusting a stimulation rate of the one or more stimulation pulses.

14. The system of claim 13, wherein the sound processor is further configured to decrease the stimulation rate in response to an increase in at least one of the tonality indices.

15. The system of claim 5, wherein the sound processor is further configured to:
generate one or more peak estimates for one or more of the analysis channels; and
adjust the one or more stimulation parameters based on at least one of the peak estimates.

16. A system comprising:
a sound processor configured to
divide an audio signal into a plurality of analysis channels each corresponding to a particular electrode included in a plurality of electrodes implanted in a patient,
generate tonality indices for each of the analysis channels in the plurality of analysis channels, the tonality indices each representing a tonality associated with one of the analysis channels;
generate one or more stimulation pulses configured to represent the audio signal in accordance with one or more stimulation parameters;
direct an implantable cochlear stimulator communicatively coupled to the sound processor to apply the one or more stimulation pulses to a stimulation site within a patient via at least one electrode; and
dynamically adjust at least one of an electrode configuration of the at least one electrode and a stimulation rate of the one or more stimulation pulses in response to a change in at least one of the tonality indices.

17. The system of claim 16, wherein the sound processor is configured to adjust the electrode configuration by focusing an excitation field produced by the at least one electrode.

18. The system of claim 17, wherein the sound processor is further configured to increase the focusing of the excitation field in response to an increase in at least one of the tonality indices.

19. The system of claim 16, wherein the sound processor is configured to adjust the electrode configuration by adjusting an amount of current steering corresponding to at least one of the one or more stimulation pulses.

20. The system of claim 16, wherein the sound processor is configured to decrease the stimulation rate in response to an increase in at least one of the tonality indices.

* * * * *